(12) United States Patent
Belfer

(10) Patent No.: US 11,002,650 B2
(45) Date of Patent: May 11, 2021

(54) PORTABLE DEVICE FOR DIRECT SHEAR EXPRESS FIELD TEST

(71) Applicant: Robert M. Schwartz, Miami, FL (US)

(72) Inventor: Boris S. Belfer, Coconut Creek, FL (US)

(73) Assignee: Robert M. Schwartz, Miami, FL (US)

( * ) Notice: Subject to any disclaimer, the term of this patent is extended or adjusted under 35 U.S.C. 154(b) by 215 days.

(21) Appl. No.: 16/096,084

(22) PCT Filed: Apr. 25, 2017

(86) PCT No.: PCT/US2017/029392
§ 371 (c)(1),
(2) Date: Oct. 24, 2018

(87) PCT Pub. No.: WO2017/189563
PCT Pub. Date: Nov. 2, 2017

(65) Prior Publication Data
US 2019/0137375 A1 May 9, 2019

Related U.S. Application Data

(60) Provisional application No. 62/326,917, filed on Apr. 25, 2016.

(51) Int. Cl.
*G01N 3/24* (2006.01)
*G01N 33/24* (2006.01)
(Continued)

(52) U.S. Cl.
CPC ............... *G01N 3/24* (2013.01); *E02D 1/00* (2013.01); *E02D 1/02* (2013.01); *E02D 1/022* (2013.01);
(Continued)

(58) Field of Classification Search
CPC .. G01N 3/24; G01N 33/24; G01N 2203/0019; G01N 2203/0025;
(Continued)

(56) References Cited

U.S. PATENT DOCUMENTS 3,406,567 A 10/1968 Terry
3,427,871 A 2/1969 Handy
(Continued)

FOREIGN PATENT DOCUMENTS

CN 201817804 U 5/2011
CN 102944486 * 2/2013 ............... G01N 3/24
(Continued)

OTHER PUBLICATIONS

Machine translation of JP 56-006819 (Year: 1981).*

*Primary Examiner* — Natalie Huls
(74) *Attorney, Agent, or Firm* — Robert M. Schwartz; Alfred K. Dassler

(57) ABSTRACT

A soil shear testing device having a frame with a first plate and a second plate spaced apart from the first plate and fixed with respect to the first plate for defining a gap therebetween, the first plate having a first plate aperture formed therein and the second plate having a second plate aperture formed therein and being coaxial with the first plate aperture. A movable plate being insertable into the gap, having a movable plate aperture formed therein, the moveable plate being insertable into the gap into a receiving position where the moveable plate aperture is coaxial with the first and second plate apertures for allowing the device to accept a soil sample column, the gap having a depth for permitting the movable plate to be displaced past the receiving position for shearing the soil sample column at two separate shearing planes defined by opposite sides of the moveable plate.

15 Claims, 13 Drawing Sheets

(51) Int. Cl.
*E02D 1/00* (2006.01)
*E02D 1/02* (2006.01)

(52) U.S. Cl.
CPC ..... *G01N 33/24* (2013.01); *G01N 2203/0019* (2013.01); *G01N 2203/0284* (2013.01)

(58) Field of Classification Search
CPC .... G01N 2203/0284; E02D 1/00; E02D 1/02; E02D 1/022
See application file for complete search history.

(56) References Cited

U.S. PATENT DOCUMENTS

| | | | |
|---|---|---|---|
| 3,494,182 | A | 2/1970 | Sutton |
| 4,149,407 | A | 4/1979 | Strom et al. |
| 4,854,175 | A | 8/1989 | Budhu |
| 4,885,941 | A * | 12/1989 | Vardoulakis ............ G01N 3/08 73/794 |
| 5,739,436 | A * | 4/1998 | Trautwein ............... G01N 3/24 73/841 |
| 6,216,531 | B1 | 4/2001 | Zhou |
| 6,834,554 | B2 | 12/2004 | Shen |
| 10,048,183 | B2 * | 8/2018 | Ni ............................ G01N 3/08 |
| 2012/0004848 | A1 | 1/2012 | Kinast et al. |
| 2019/0178763 | A1 * | 6/2019 | Chitu ................ B29C 66/73921 |
| 2020/0249139 | A1 * | 8/2020 | Yu .......................... G01N 33/24 |

FOREIGN PATENT DOCUMENTS

| | | |
|---|---|---|
| CN | 102944486 B | 1/2015 |
| JP | S56-6819 A | 1/1981 |

* cited by examiner $$F = \frac{\sum(c + \sigma \tan\varphi) \cdot l}{\sum W \sin\alpha}$$

Where

F - factor of safety c - cohesion, $\varphi$ - angle of internal friction

W - total weight of slice $\alpha$ - angle of slice base $l$ - lenght of slice base

PORTABLE DEVICE FOR DIRECT SHEAR EXPRESS FIELD TEST

This application claims the priority from PCT application PCT/US2017/029392, filed Apr. 25, 2017, entitled Portable Device for Direct Shear Express Field Test and U.S. Provisional Patent Application Ser. No. 62/326,917, filed on Apr. 25, 2016, entitled Portable Device for Direct Shear Express Field Test, this prior application is herewith incorporated by reference in its entirety.

BACKGROUND OF THE INVENTION

Engineers frequently need to test physical soil parameters in order to calculate slope stability. Existing devices apply a vertical load, then find maximum corresponding horizontal load which causes failure. By changing a load acting upon the sample and plotting points of normal stress σ (Sigma), shear stress τ (Tau), and drawing a failure envelope line through them—cohesion and angle of internal friction may be determined—using the Mohr-Coulomb formula, as described in ASTM D 3080-98. (ASTM Designation: D 3080-98 entitled "Standard Test Method for Direct Shear Test of Soils Under Consolidated Drained Conditions" published by ASTM, 100 Barr Harbor Drive, PO Box C700, West Conshohocken Pa. 19428-2959 www.astm.org). Existing laboratory direct shear test machines have significant size, with table top machines being 30 to 44 inches in length, are heavy, with a weight or 140 to 180 pounds are relatively expensive $12,000 and are essentially immobile. These machines typically have carriage movement, required by known arrangement of the machine, which necessarily introduces errors, due in large measure to the friction of the carriage wheels when high vertical loads are imposed. Moreover, there is a lower limit of horizontal displacement, usually about one ten-thousandth of an inch, below which, surface finish limitations prevent meaningful readings from being obtained.

As practiced in the art, soil properties for one type of material need to be determined only once. However, on one construction site location different soil types may be found at different depths. Within one site different soil types may be present at different locations at the site. When these different soil types are encountered, testing must be performed to ensure safety, which means equipment and operators are idle waiting for authorization from the job site professional engineer that it is safe to proceed. The present invention greatly reduces costs which were previously accrued due to the testing requirements. The present invention is a portable soil testing device, that does not require electricity or batteries, that is implemented at the job site and satisfies the long felt need which was recognized, persistent and not solved by others to evaluate soil conditions at the construction site or other remote location quickly and easily.

BRIEF SUMMARY OF THE INVENTION

The present invention is a portable device that in case of testing soft or granular materials can be manufactured from light weight plastic (less than pound), it is small in size (in a preferred embodiment approximately 3 inch×3 inch×3 inch) and relatively inexpensive to manufacture. This present invention will allow a user to perform express field tests during preliminary site exploration for development, repair, or maintenance, sub-surface exploration, space missions to other planets, disaster relief, emergency works, sapper (combat engineering), and quality control of materials delivered on site, construction excavation, dredging, or embankment/dam works to help provide early identification of slope failure possibility. Excavation at construction sites, in particular, is recognized as one of the most hazardous construction operations. Occupational Safety and Health Administration (OSHA) has revised Subpart P, Excavations, of 29 CFR 1926.650, 29 CFR 1926.651, and 29 CFR 1926.652 to make the standard easier to understand, permit the use of performance criteria where possible, and provide construction employers with options when classifying soil and selecting employee protection methods—to utilize different soil testing techniques and quoting the sloping and benching of sides as number one suggested method. These requirements are also reflected in the National Bureau of Standards Report BSS-121 as preferred by contractors.

The present invention uses two commercially available dial pocket penetrometers, further used as dynamometers, to apply and measure compression force (perpendicular to the shearing plane) and shear force (parallel to the shearing plane). Such a pocket penetrometer is manufactured by Humboldt Mfg. Co., 875 Tollgate Road, Elgin, Ill. 60123 USA, model H-4205 Soil Penetrometer, Dial Type, which includes an adapter foot.

Though the accuracy of this portable device of the present invention, cannot be compared with commercial models, the present invention utilizes two shearing surfaces instead of one and the compression force or load does not transfer to a moving part as in conventional apparatus, therefore it is believed that the accuracy of calculations of the present invention may increase proportionally to the number of measured samples (minimum 4 are recommended).

A prototype device was tested using cleaned dry coarse sand from Fort Lauderdale Beach, Fla., USA, having zero cohesion angle of internal friction 32 degrees. The same dry course sand material was previously tested on a conventional direct shear machine, model Humboldt HM-2300.020.

In this test, vertical step loads were 5, 10, 15 and 20 pounds, applied over round 25 millimeters diameter (0.005284 sf) adapter foot producing corresponding pressures of 946, 1892, 2838 and 3785 per square foot. The forces required to shear four samples referenced above, under loads accordingly were 5, 13, 16 and 24 pounds, applied over 2 round 25 millimeters diameter surfaces, produced shear stresses of 473, 1230, 1514 and 2271, which were linearly correlated to 30 degree angle—more conservative result (flatter angle) than obtained from commercial machine, calibrated by the manufacturer of the commercial machine Humboldt HM-2300.020.

The approximate six percent (6%) discrepancy may be attributed to behavior of a larger sample used by a commercial grade machine which could have contamination by smaller particles or there could be minor variations of load applied by hand and dial gauge readings on the hand-held pocket penetrometer devices.

In the inventor's opinion, the test purposes were achieved by reasonably proving validity of the concept implemented within the prototype device of the present invention. Additional testing can be performed to find uniformity coefficient for different samples.

With the present invention, the soil testing can now be performed at the job site, without having to transport the soil sample from a remote location to where the test equipment is located. Further, the testing of multiple soil samples can now be performed quickly at the job site, using the present invention, and the test readings can be calculated at the job site or by engineers based on data obtained from the remote location/job site, timely, with reasonably accurate results.

Use of the present invention at the job site reduces the previous time it took to get test results and with the reduced time to test the soil, workers do not have to be idle at the job site while waiting for test results and expensive machinery and equipment will not remain idle. Thus, the safety of the workers, preservation of equipment and the integrity of the job site can be maintained quickly and efficiently, with on job site testing and measuring capabilities provided by the present invention.

It is accordingly an object of the invention to provide a soil shear testing device having a frame with a first plate and a second plate spaced apart from the first plate and fixed with respect to the first plate for defining a gap therebetween, the first plate having a first plate aperture formed therein and the second plate having a second plate aperture formed therein and being coaxial with the first plate aperture, a movable plate being insertable into the gap, the moveable plate having a movable plate aperture formed therein, the moveable plate being insertable into the gap into a receiving position where the moveable plate aperture is coaxial with the first and second plate apertures for allowing the device to accept a soil sample column, the gap having a depth for permitting the movable plate to be displaced past the receiving position for shearing the soil sample column at two separate shearing planes defined by opposite sides of the moveable plate.

With the foregoing and other objects in view there is provided a moveable plate having a sliding fit in the gap with respect to a thickness of the moveable plate.

In accordance with another feature of the invention the first plate aperture is a blind hole facing the gap.

In accordance with an added feature of the invention the second plate aperture is a through hole.

In accordance with an additional feature of the invention a plunger tip is configured for being mounted onto a penetrometer, the plunger tip being dimensioned to fit into the second plate aperture with clearance between the plunger and the aperture for applying a compression load onto the soil sample column during a soil shear test.

In accordance with yet another added feature of the invention the moveable plate has a receptacle formed therein, the receptacle being dimensioned for accepting a tip of a penetrometer during the soil shear test.

With the foregoing and other objects in view there is further provided a soil shear testing device having a first plate having a first plate sliding surface, the first plate having a blind hole formed therein opening out in the first plate sliding surface, a movable plate having a movable plate sliding surface being slideable along the first plate sliding surface in a testing direction for defining a first shearing plane, the moveable plate having a through hole formed therein, a second plate spaced apart from the first plate and fixed with respect to the first plate, the second plate spaced apart from the first plate sliding surface for defining a gap therebetween, the gap being sized for insertion of the movable plate therein, the second plate having a second plate through hole formed therein being coaxial with the blind hole, the second plate and the moveable plate defining a second shearing plane therebetween, a guide guiding the moveable plate with respect to the first plate along the testing direction into a sample loading position in which the through hole is axially aligned with the blind hole and the second plate through hole, in which a soil sample column is loaded into the second plate through hole, the through hole and the blind hole, the guide guiding the moveable plate during displacement of the moveable plate with the through hole past the loading position for shearing the soil sample column at the first and second shearing planes.

In accordance with another feature of the invention a plunger tip is configured for being mounted onto a dynamometer, the plunger tip being dimensioned to being inserted into the through hole and applying a compression force onto the soil sample column during a soil shear test.

In accordance with an added feature of the invention a moveable plate has a receptacle formed therein, the receptacle being dimensioned for accepting a tip of a further dynamometer during the soil shear test.

In accordance with an additional feature of the invention a rod standard is dimensioned for being inserted into the through hole, the rod standard having a defined weight for applying a predetermined compression load onto the soil sample column during the soil shear test.

In accordance with yet another feature of the invention is a predefined weight, the rod standard constructed for having the further predefined weight affixed and carried thereon during the soil shear test.

12. In accordance with still another feature of the invention is a wall connecting the first plate to the second plate and setting a height of the gap, the wall being parallel to the testing direction and defining a guide surface of the guide.

In accordance with an added feature of the invention, a wall is disposed for limiting a travel of the moveable plate in the testing direction when the soil column sample has been sheared during the soil shear test.

With the foregoing and other objects in view there is also provided a soil shear testing device with a first plate having a blind hole formed therein, the blind hole delimited by a first plate shearing surface in which the first plate blind hole opens out, a second plate having a second plate hole delimited by a second plate shearing surface in which the second plate hole opens out, the second plate being fixedly mounted to the first plate with the blind hole coaxially disposed with the second plate hole and with the first plate shearing surface spaced apart from the second plate shearing surface at a distance defining a gap therebetween, a moveable plate having a first moveable plate shearing surface and a second moveable plate shearing surface opposite the first moveable plate shearing surface, the moveable plate having a moveable plate through hole delimited by the first moveable plate shearing surface and by the second moveable plate shearing surface, the movable plate dimensioned for being inserted into the gap in an insertion direction and for defining a first shearing plane between the first plate shearing surface and the first moveable plate shearing surface and for defining a second shearing plane between the second plate shearing surface and the second movable plate shearing surface, the moveable plate being displaceable in the gap in the insertion direction into a soil sample loading position in which the moveable plate through hole is coaxially aligned with the blind hole and the second plate hole.

With the foregoing and other objects in view there is further provided a method of testing a soil sample by providing the soil shear testing device disclosed herein and placing the moveable plate in the receiving position, loading a soil sample into the device through the second plate aperture until the soil sample column is provided, applying a substantially constant compression load on the soil sample column, subsequent to applying the substantially constant load, applying an incrementally increasing compression load with a dynamometer on the moveable plate until the soil sample column fails and is sheared by the moveable plate, determining the maximum value of the incrementally increasing compression load by reading the maximum value reached by the dynamometer.

DETAILED DESCRIPTION OF THE PREFERRED EMBODIMENT

Figure 1:
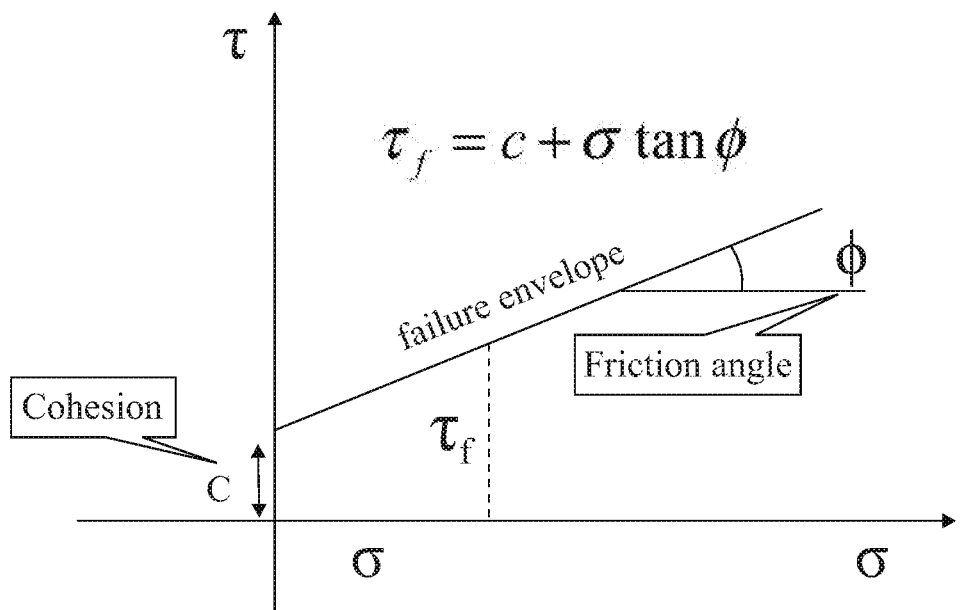
FIG. 1 is a diagram of the Mohr-Coulomb formula showing failure criterion in terms of total stress.
Figure 1A:
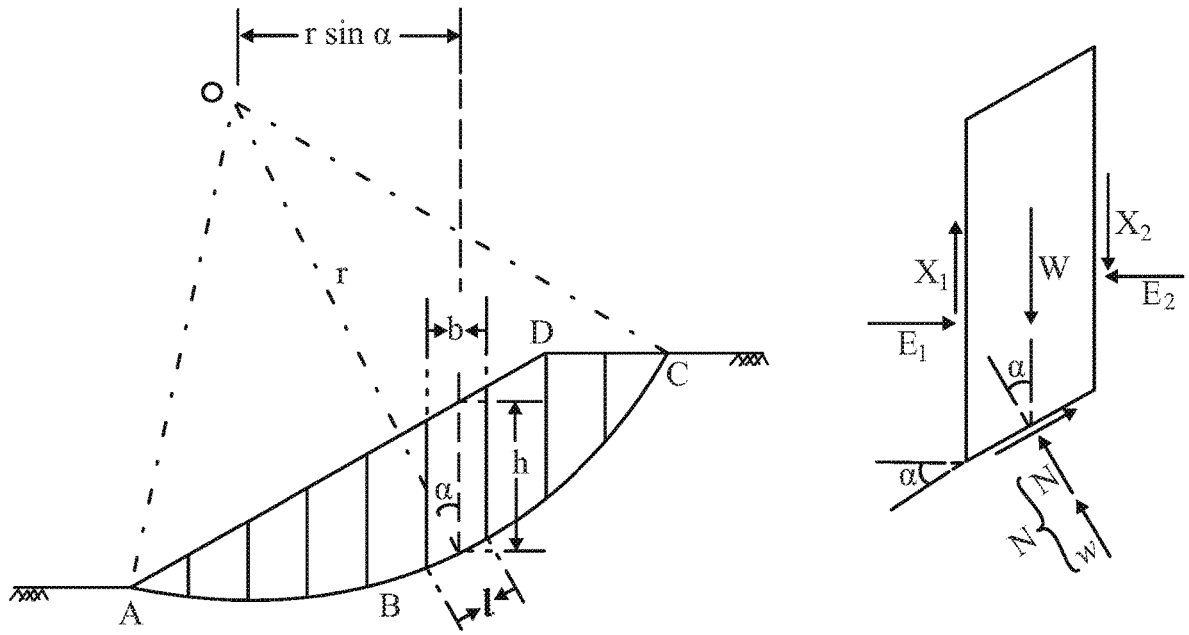
FIG. 1A shows factor of safety formulas and graphs as known in the art.
Figure 2:
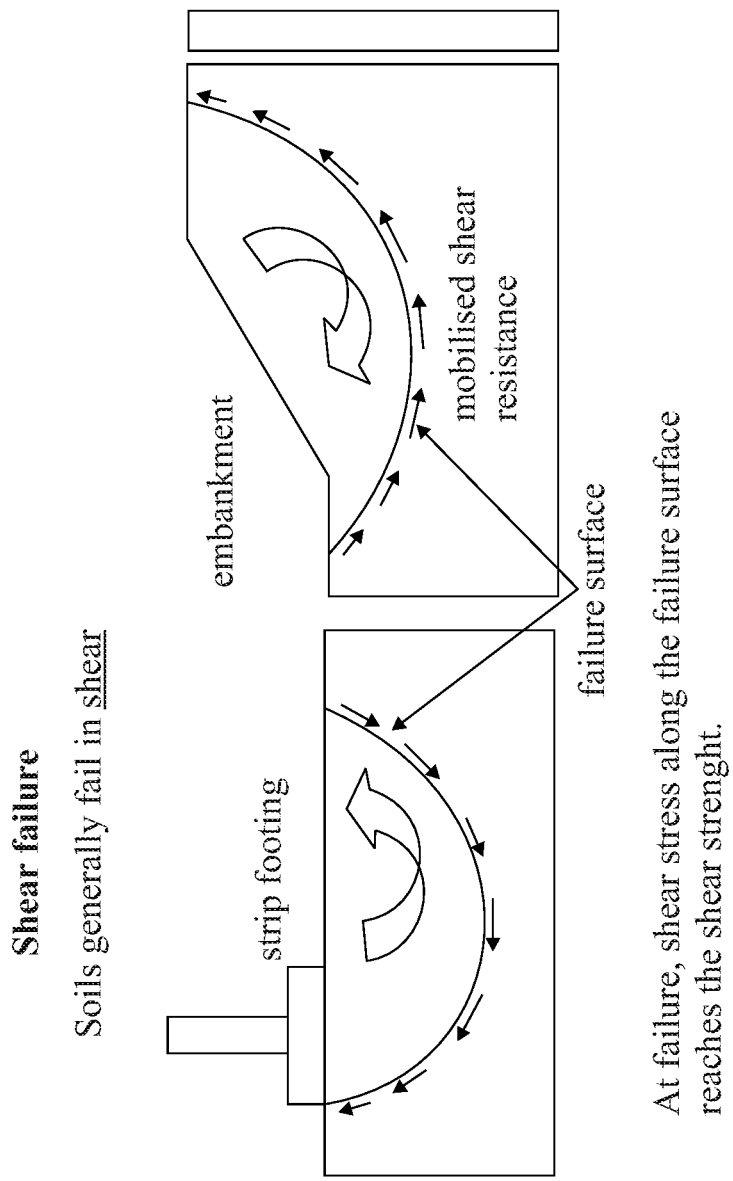
FIG. 2 is a diagram showing shear failure, for strip footing and for an embankment.

The present invention is a portable field test shear device 10 to measure the maximum shear stress a sample soil material 51 can take without failure. The shear device 10 has a shear box frame 20 and a shear slide moveable plate 40 that is inserted into the frame 20 in an insertion/testing direction TD.

Frame 20 has a first plate 25 and a second plate 26. First plate 25 and second plate 26 are connected by lateral walls 21, which are substantially parallel to the insertion/testing direction TD. A rear wall 23 may be provided orthogonal to the insertion/testing direction TD. The rear wall 23 can be provided as a projection which limits the travel of the movable plate 40 which does not entirely cover a rear side of the frame 20. Frame 20 is preferably of a solid material of plastic, wood, metal or any other material, though portions thereof may be hollow.

First plate 25 and second plate 26 are spaced apart by a gap 61 between the first plate 25 and the second plate 26 for receiving the moveable plate 40 therein. First plate 25 has a first plate blind hole or aperture 67 and second plate 26 has a second plate through hole or aperture 65. The blind hole 67 is cylindrical and opens out into a first plate sliding or shearing surface 85 on which the movable plate 40 slides. The second plate through hole 65 is cylindrical and opens out into a second plate sliding or shearing surface 86 on which the movable plate 40 slides. First plate blind hole 67 has a bottom surface 69. Though not shown, it is possible to add drainage openings extending from blind hole 67 to an exterior edge of frame 20, for any water or liquid in a soil sample material 51 to drain from the soil sample material 51 into and through drainage openings in blind hole 67 and out of the frame 20. Second plate through hole 65 is a cylindrical through hole that defines a soil sample loading passage into a soil sample receiving cavity 60.

Moveable plate 40 is inserted into the gap 61 in the insertion/testing direction TD and is slideable within gap 61, and is removable from gap 61. The lateral walls 21 delimit the gap 61 and serve as a lateral guide that guides the moveable plate 40 along the insertion/testing direction TD by guiding lateral sides 43 of movable plate 40. The lateral guide may alternatively be provided as mating male and female profiles on the moveable plate 40 and one of the first and second plates 25 and 26 which extend parallel to the insertion testing direction. The mating male and female profiles may have any type of cross section that will ensure lateral stability such as rectangular, square, triangular, semicircular etc. Moveable plate 40 has a first sliding or shearing surface 95 and a second sliding or shearing surface 96 opposite the first sliding surface 95. There is sufficient clearance for a sliding fit between the sliding surfaces 95 and 96 of moveable plate 40 and corresponding surfaces 85 and 86 of the first and second plates 25 and 26 that define the gap 61. A sliding fit is considered as a fit in which the moveable plate 40 freely slides without any interference to the moveable plate 40 by the first and second plates 25 and 26 (i.e. there is clearance between the moveable plate and the first and second plate along the sliding surfaces 85, 86, 95 and 96 and the movable plate 40 does not bind in the gap 61). Moveable plate 40 has a moveable plate through hole or aperture 66 that opens out in the first sliding surface 95 and the second sliding surface 96. The moveable plate through hole 66 may be cylindrical.

Figure 10:
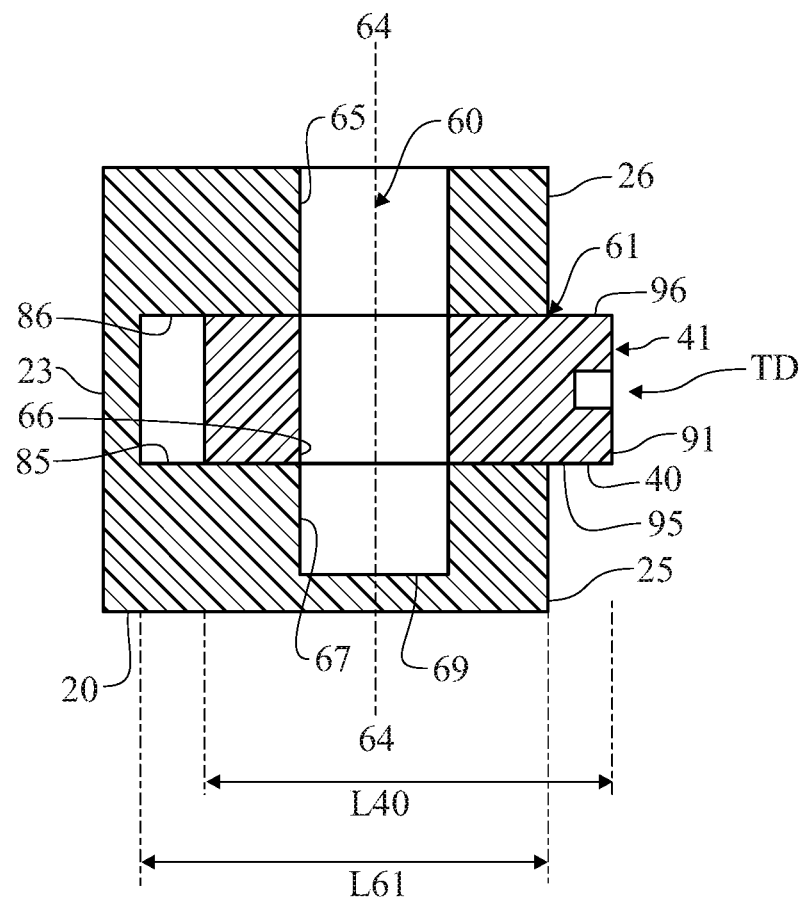
FIG. 10 is a cross section of the frame and movable plate in the receiving position the first plate, second plate and movable plate holes aligned.

As seen in FIG. 10, the soil sample receiving cavity 60 is defined by aligning the moveable plate hole 66 to be coaxial with the first plate hole 67 and the second plate hole 65, where the first plate hole 67 and the second plate hole 65 are permanently coaxial with one another, due to their formation in the respective plates 25 and 26. The soil sample cavity 60, is ready to receive a sample soil material 51 when the hole 66 of the moveable plate 40 is moved into longitudinal alignment with the holes 65 and 67 along longitudinal axis 64. When the moveable plate hole 66 is aligned the moveable plate 40 is in a receiving position 41 shown in FIGS. 6,7,8, 10 and 11.

Figure 3:
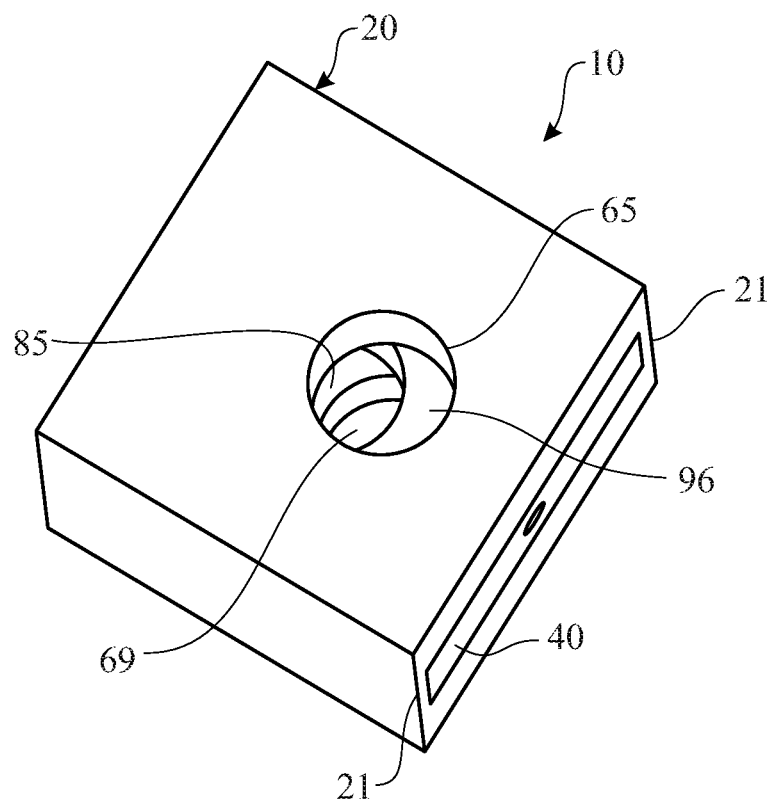
FIG. 3 is a top perspective view of the device of the present invention without soil.
Figure 4:
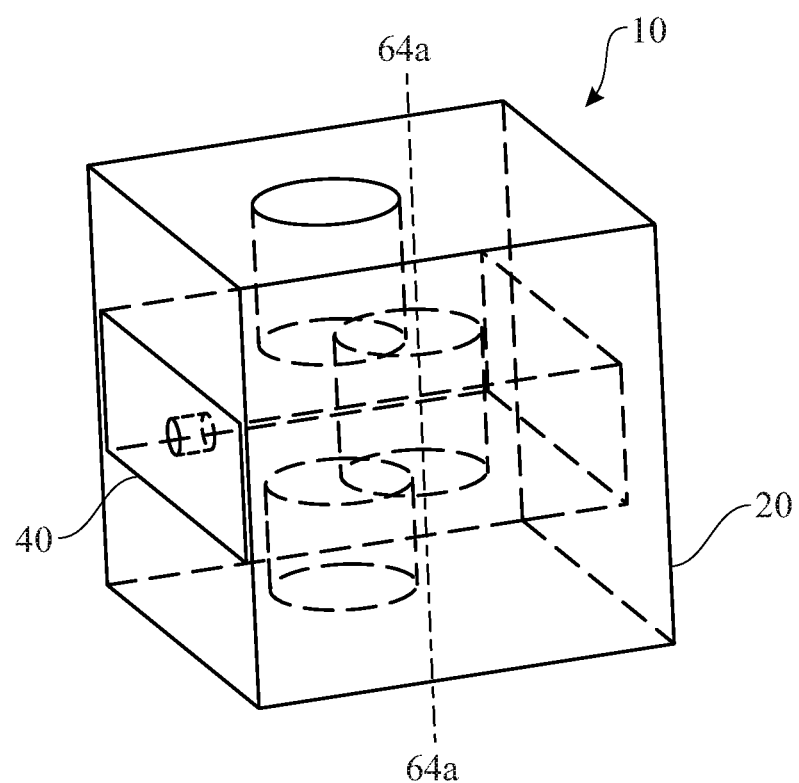
FIG. 4 is a front side perspective view of the device of the present invention showing in dashed lines inner portions of the invention.
Figure 5:
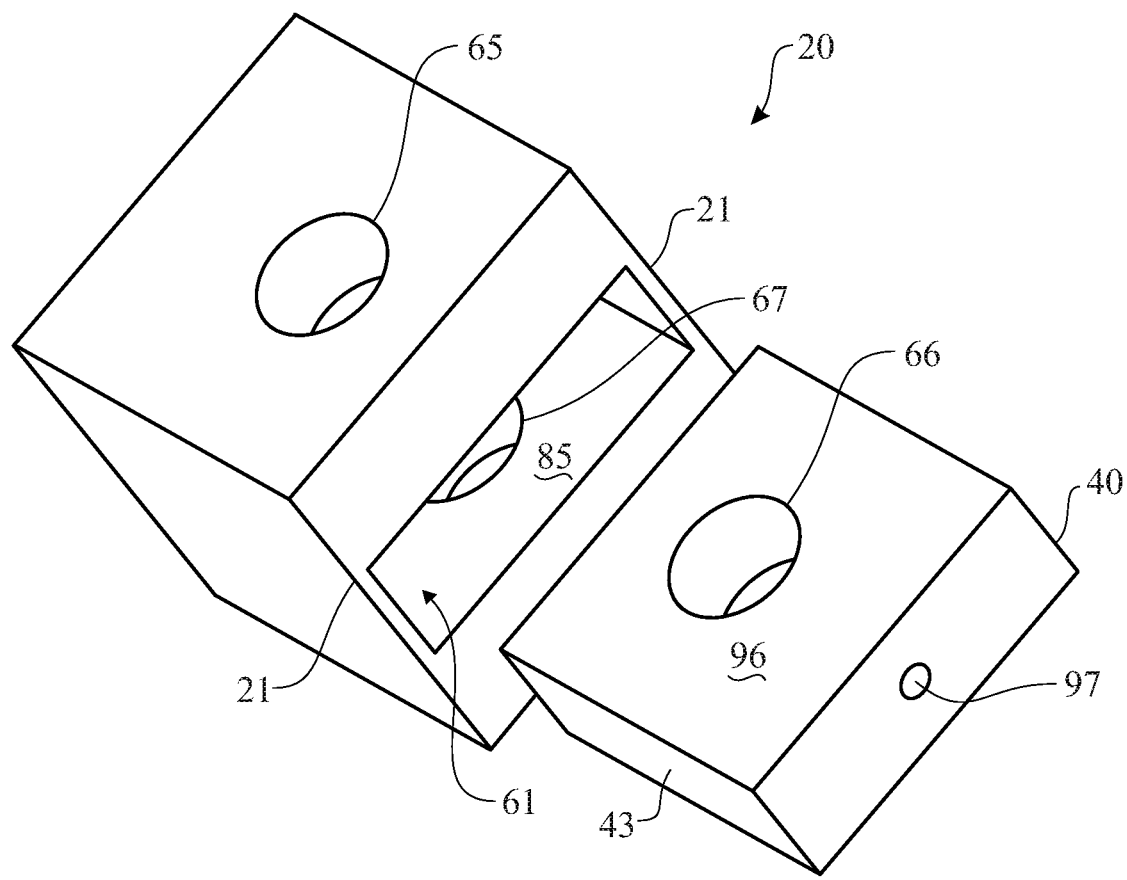
FIG. 5 is a top perspective view of the invention showing the movable plate removed from the frame.
Figure 6:
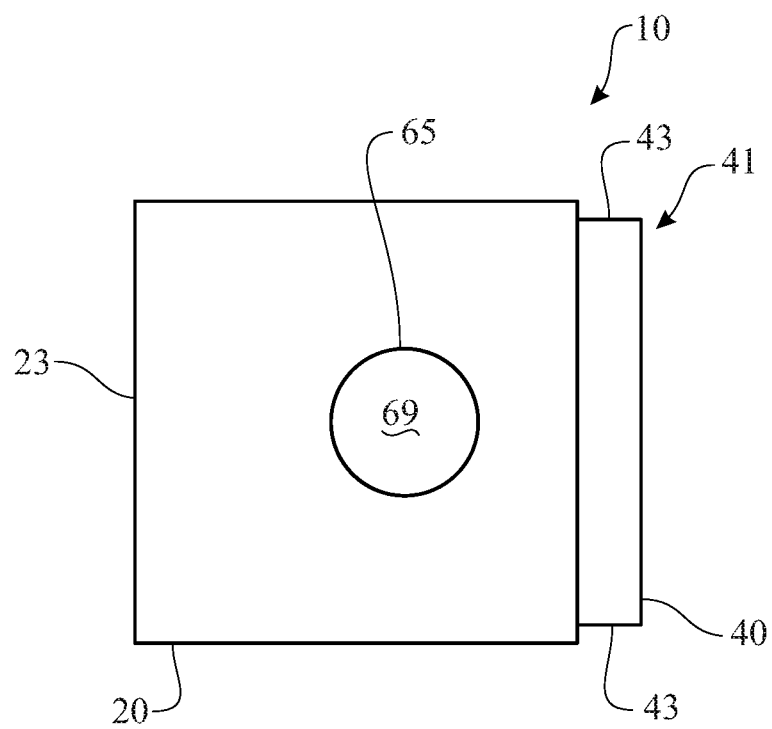
FIG. 6 is a top view of the device with the bores aligned showing the movable plate in the receiving position.
Figure 7:
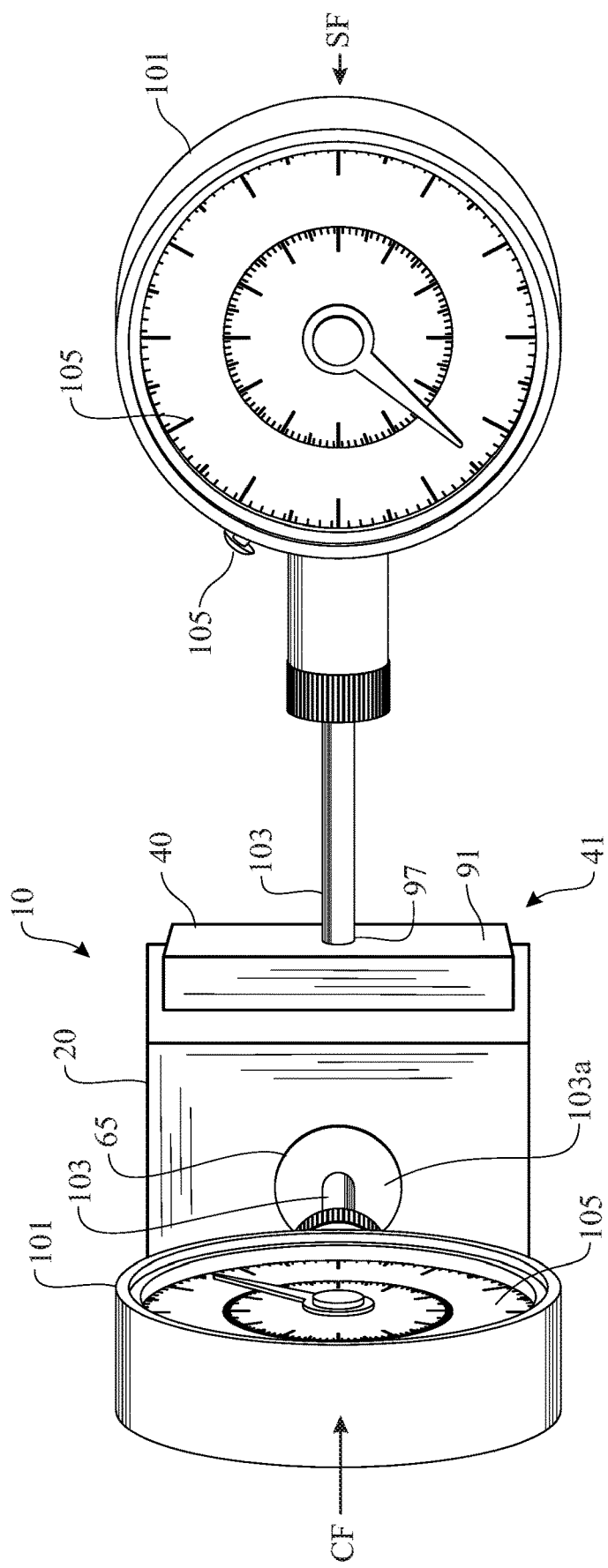
FIG. 7 is a top perspective view of the device in use showing two pocket penetrometers affixed to the device in the receiving position before the soil is sheared.
Figure 12:
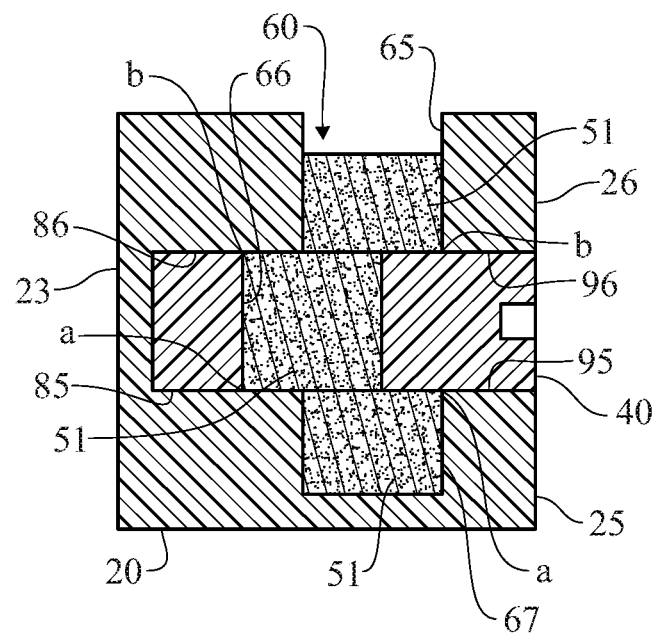
FIG. 12 is a cross section of the frame and moveable plate and soil sample column after the soil sample column has failed and has been sheared along the two shear planes.

As shown in FIG. 10, the length L40 of moveable plate 40 is substantially equal to the interior length or depth L61 of gap 61. FIGS. 3, 4 and 12, show the position of the moveable plate 40 after the soil sample column 50 has been sheared and the movable plate 40 has been moved to a position in the testing direction TD in which a longitudinal axis 64a of the moveable plate hole 66 has been moved past the longitudinal axis 64 of the soil sample receiving cavity 60. If a compression force to shear the soil sample column 50 is great enough, the rear wall 23 serves as a stop to limit the travel of movable plate 40.

Two pocket penetrometers 101, or dynamometers 101 can be used as one or both of the penetrometers 101, to measure the compression forces that are applied to the soil sample column 50 to provide the values of the shear measurements that are used to calculate slope stability. A first dynamometer 101 has a dial 105 and a plunger tip 103 with an adapter foot 103a. The adapter foot 103a is slightly smaller in diameter than the diameter of the second plate hole 65 to allow the adapter foot 103a to freely slide (no frictional losses) within the second plate hole 65. It is desirable that the adapter foot 103a be sized so that the adapter foot 103a is as large as possible without rubbing or binding in the second plate hole 65. A second dynamometer 101 has a dial 105 and a plunger tip 103. For the second dynamometer 101, the plunger tip 103 engages and fits within a receptacle 97 formed in a front wall 91 of moveable plate 40. The dials of each dynamometer 101 provide scaled measurements to measure force. Each dynamometer has a release button 105. The release button 105 on first dynamometer 101 is hidden in the given view.

Figure 8:
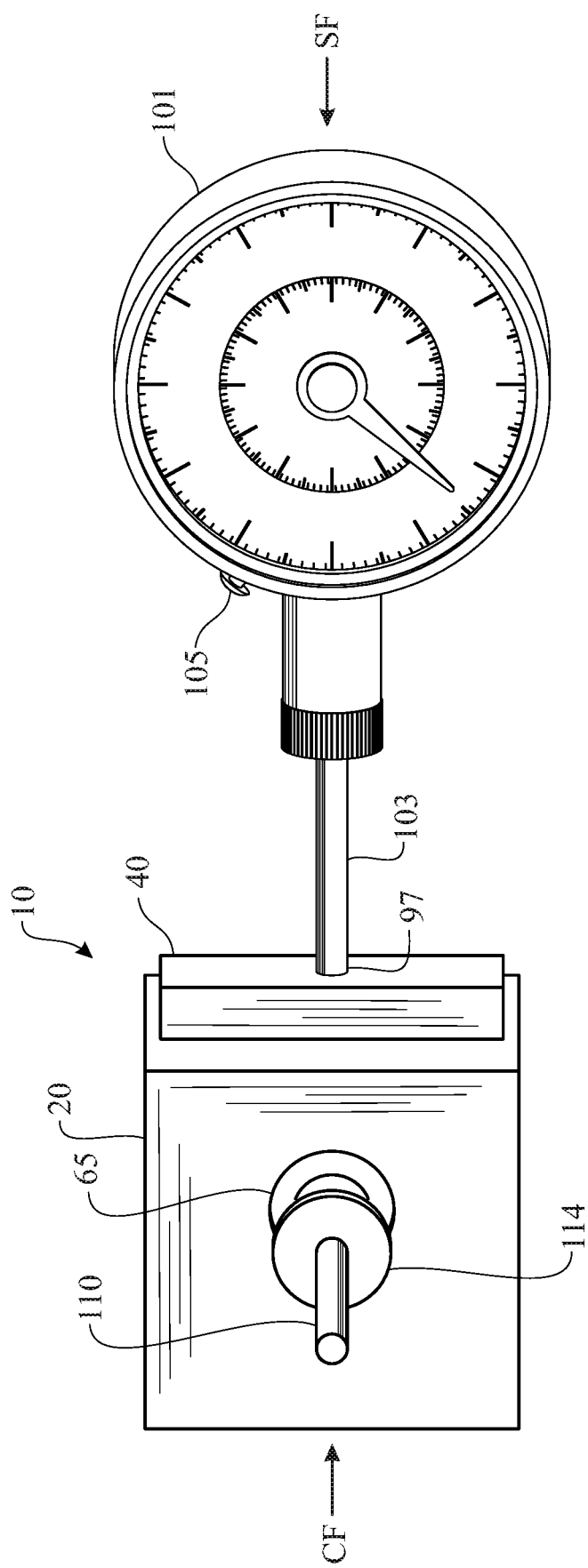
FIG. 8 is a top perspective view of the device showing use of a rod standard for applying a fixed compression force at the soil sample receiving cavity before the soil is sheared.
Figure 9:
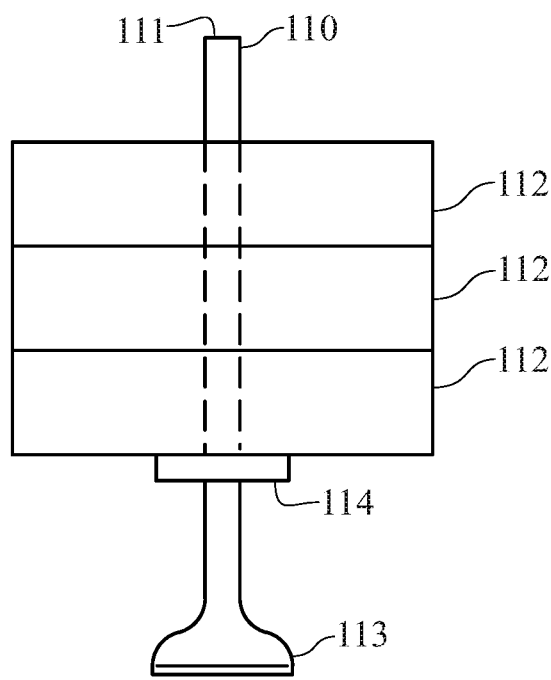
FIG. 9 is a side view of the rod and footer, loaded with individual weights for asserting the fixed compression force.

As shown in FIGS. 8 and 9, instead of a dynamometer 101, the compression force CF can also be provided by a rod standard 110 of a defined weight. The rod standard 110 is constructed to carry additional weights 112 thereon for obtaining multiple shear stresses. The additional weights 110 slideably fits onto a first end 111 of rod standard 110. A shoulder 114 supports the weights 112 and spaces the weights from the second plate 26. The second end 113 of rod 110 is dimensioned to have a slip fit in the second plate hole 65. This arrangement will load the soil sample 51 within the soil sample receiving cavity 60 with a fixed amount of weight or force, which can be controlled according to the quantity of fixed weights 112 attached. As shown in FIG. 8 the compression force is adjusted by one or more weights 112 that slide onto the rod 110. The compression force CF is fixed at a predetermined weight, based on the amount of weight attached to rod 110 and thus this compression force CF is known as a fixed quantity of weight/force to be used within the formula equations. An advantage of using a fixed weight or predetermined weight for the compression force CF is there is only one variable to be measured by a dynamometer, namely the second compression force SF of the dynamometer 101. To obtain multiple data points, the test can be repeated multiple times each time with a different fixed weight, e.g. if the rod and the weights were each two pounds, then the test could be performed at 2, 4, 6 or 8 pounds of compression force, each time increasing the force by 2 pounds.

The device 10 is light, portable and thus can be used in field conditions. To operate the device 10, no electricity, complicated machinery, hydraulics, fluids or pneumatic compressors of any kind are required. First, the movable plate 40 is inserted into the gap 61 to the receiving position 41, such that frame 20 and the longitudinal axis 64 are aligned by sliding movable plate 40 within gap 61 such that the second plate aperture 65 is visibly aligned with the first plate aperture 67 and the moveable plate aperture 66.

Subsequently, a sample of soil material 51 to be tested is loaded into soil sample receiving cavity 60 forming soil sample column 50. As known in the art and specified by engineering test protocol, the sample soil column 50 is properly loaded, and may be compacted in the soil sample receiving cavity 60. Then the first dynamometer 101 is placed in position so that the adapter foot 103a is within the second plate hole 65 against the soil sample column 50 within the soil sample receiving cavity 60. Then a desired constant compression force, CF, is applied against the first dynamometer 101 (along axis 64, i.e. normal force) until a desired constant force is applied against the sample soil column 50 as indicated on the dial 105 of the first dynamometer 101. Alternatively, the rod standard 110 is inserted within the second plate hole 65 against the soil sample column 50 within the soil sample receiving cavity 60. Then the second dynamometer 101 is inserted into receptacle 97, a second compression force SF is applied against movable plate 40 (perpendicular to the longitudinal axis 64, ie. shear force) with second dynamometer 102. The user maintains a constant compression force CF while slowly increasing the second compression force SF with the second dynamometer until the soil sample column 50 fails and is sheared along shear planes defined along the moveable plate sliding surfaces 95 and 96. Upon failure the second dynamometer freezes and maintains the value of the maximum force applied to the second dynamometer (the force at which the column 50 is sheared), which is subsequently read from the second dynamometer dial. The values from each dynamometer dial 101 (or the rod standard 110 weight) and 102 are read and recorded. Then the value for the constant compression force CF is used to calculate the normal stress with the equation $\sigma=CF/A$, where A is the cross-sectional area of the sample column 50. Likewise, the value for the shear force SF is used to calculate the shear stress with the equation $\tau=SF/2A$ where A is the cross sectional area of the sample column 50. These values $\sigma$ and $\tau$ and any additional calculations, are then plotted using the Mohr-Coulomb Failure Criterion shown on FIG. 1. to calculate the failure envelope and friction angle, as known in the art. There are existing applications for mobile devices to make these calculations for slope stability analysis, simple slope, and likewise programs exist for use on desktop/laptop computers (Rocscience Slide—Rocscience Inc., 54 St. Patrick St., Toronto, ON M5T 1V1), utilizing formulas in FIG. 1 to calculate the shear failure criteria and subsequent derivations in FIG. 1.A for factor of safety as known in the art. After the measurements are taken from the dials of the dynamometers 101 and 102, a release button 105 resets the dials back to zero for the next set of readings. Theoretically, measurements shall be repeated to obtain at least two pairs of normal stress and shear stress values ($\sigma_1$, $\tau_1$ and $\sigma_2$, $\tau_2$) in order to draw a failure envelope line through two points, but on practice more points are recommended to make possible statistical analysis for quality control. For the purpose of obtaining additional data points, the compression force applied at each following sample is incrementally increased and corresponding shearing force is recorded. These incremental increases of compression force are made by applying additional compression force by the operator on dynamometer 101 or additional weight can be placed on rod 110 as heretofore described.

The present device 10 tests the direct shear of the soil along two shearing surfaces by applying compression force CF and shearing force SF loads perpendicular to one another, which divided by surface area allows to calculate corresponding vertical stress and horizontal shear during the critical state (failure) condition. Each of such dynamometers retains the maximum force asserted at the critical state of failure. Result values are plotted on $\tau$-$\sigma$ chart (FIG. 1) by a qualified professional.

Though the present device 10 shows use of a cylindrical bore for housing the soil sample, other shapes such as square can be used.

Figure 11:
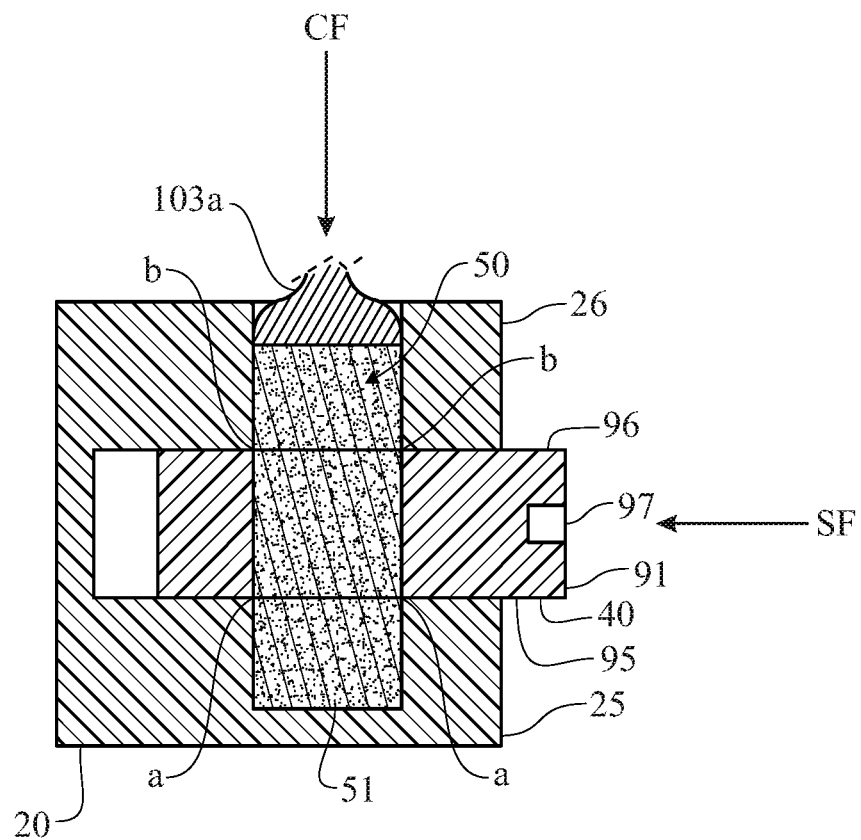
FIG. 11 is a cross section of the frame and moveable plate in the receiving position showing the soil sample column in the soil sample receiving cavity marked with the adapter footer of a dynamometer in place, alternatively the adaptor footer could be the second end of the rod standard.

It can be specially noted in the device 10 that there are two planes where the soil is simultaneously sheared, at the shearing surfaces of moveable plate 40 at a-a and b-b in FIGS. 11 and 12. This may improve the accuracy of the measurements, avoiding soil sample collapse due to accidental irregularities unintentionally created during preparation of test sample—even further increasing precision of the measurements in this device 10. Since the compression load CF is applied directly to the soil sample material 51, instead of to a plate, a majority of load (approximately 90%) from the dynamometer 101 or the rod standard 110 is not transferred onto the sliding or shearing surfaces of the movable plate 40, significant errors due to friction, which are present in shear testing devices of the prior art, are eliminated by the tri-plate construction of the present invention.

In addition to testing the shear failure of soils, additional items can be tested such as cheeses, dairy products, fruits to determine picking and shipping times.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A soil shear testing device comprising:
a frame having a first plate and a second plate spaced apart from said first plate and fixed with respect to said first plate for defining a gap therebetween, said first plate having a first plate aperture formed therein and said second plate having a second plate aperture formed therein and being coaxial with said first plate aperture;
a movable plate being insertable into said gap, said moveable plate having a movable plate aperture formed therein, said moveable plate being insertable along a testing direction into said gap into a receiving position where said moveable plate aperture is coaxial with said first and second plate apertures for allowing the device to accept a soil sample column, said gap having a depth for permitting said movable plate to be displaced past said receiving position for shearing the soil sample column at two separate shearing planes defined by opposite sides of said moveable plate;
a guide guiding said movable plate during displacement of said moveable plate with said movable plate aperture past said receiving position for shearing the soil sample column at said shearing planes; and
a wall connecting said first plate to said second plate and setting a height of said gap, said wall being parallel to said testing direction and defining a guide surface of said guide.

2. The soil shear testing device according to claim 1, wherein said moveable plate has a sliding fit in said gap with respect to a thickness of said moveable plate.

3. The soil shear testing device according to claim 1, wherein said first plate aperture is a blind hole facing said gap.

4. The soil shear testing device according to claim 3, wherein said second plate aperture is a through hole.

5. The soil shear testing device according to claim 4, further comprising a plunger tip configured for being mounted onto a penetrometer, said plunger tip being dimensioned to fit into said second plate aperture with clearance between said plunger and said aperture for applying a compression load onto the soil sample column during a soil shear test.

6. The soil shear testing device according to claim 1, wherein said moveable plate has a receptacle formed therein, said receptacle dimensioned for accepting a tip of a penetrometer during the soil shear test.

7. A method of testing a soil sample comprising:
providing the testing device according to claim 1;
placing the moveable plate in the receiving position;
loading a soil sample into the device through the second plate aperture until the soil sample column is provided;
applying a substantially constant compression load on the soil sample column;
subsequent to applying the substantially constant load, applying an incrementally increasing compression load with a dynamometer on the moveable plate until the soil sample column fails and is sheared by the moveable plate;
determining the maximum value of the incrementally increasing compression load by reading the maximum value reached by the dynamometer.

8. A soil shear testing device comprising:
a first plate having a first plate sliding surface, said first plate having a blind hole formed therein opening out in said first plate sliding surface;
a movable plate having a movable plate sliding surface being slideable along said first plate sliding surface in a testing direction for defining a first shearing plane, said moveable plate having a through hole formed therein;
a second plate spaced apart from said first plate and fixed with respect to said first plate, said second plate spaced apart from said first plate sliding surface for defining a gap therebetween, said gap being sized for insertion of said movable plate therein, said second plate having a second plate through hole formed therein being coaxial with said blind hole, said second plate and said moveable plate defining a second shearing plane therebetween;
a guide guiding said moveable plate with respect to said first plate along said testing direction into a sample loading position in which said through hole is axially aligned with said blind hole and said second plate through hole, in which a soil sample column is loaded into said second plate through hole, said through hole and said blind hole, said guide guiding said movable plate during displacement of said moveable plate with said through hole past said loading position for shearing the soil sample column at said first and second shearing planes.

9. The soil shear testing device according to claim 8, further comprising a plunger tip configured for being mounted onto a dynamometer, said plunger tip being dimensioned to being inserted into said through hole and applying a compression force onto the soil sample column during a soil shear test.

10. The soil shear testing device according to claim 9, wherein said moveable plate has a receptacle formed therein, said receptacle dimensioned for accepting a tip of a further dynamometer during the soil shear test.

11. The soil shear testing device according to claim 8, further comprising a rod standard dimensioned for being inserted into said through hole, said rod standard having a defined weight for applying a predetermined compression load onto the soil sample column during the soil shear test.

12. The soil shear testing device according to claim 11, further comprising a further predefined weight, said rod standard constructed for having said further predefined weight affixed and carried thereon during the soil shear test.

13. The soil shear testing device according to claim 8, further comprising a wall connecting said first plate to said second plate and setting a height of said gap, said wall being parallel to said testing direction and defining a guide surface of said guide.

14. The soil shear testing device according to claim 13, further comprising a further wall disposed for limiting a travel of said moveable plate in said testing direction when the soil column sample has been sheared during the soil shear test.

15. A soil shear testing device comprising:
- a first plate having a blind hole formed therein, said blind hole delimited by a first plate shearing surface in which said first plate blind hole opens out;
- a second plate having a second plate hole delimited by a second plate shearing surface in which said second plate hole opens out, said second plate being fixedly mounted to said first plate with said blind hole coaxially disposed with said second plate hole and with said first plate shearing surface spaced apart from said second plate shearing surface at a distance defining a gap therebetween;
- a moveable plate having a first moveable plate shearing surface and a second moveable plate shearing surface opposite said first moveable plate shearing surface, said moveable plate having a moveable plate through hole delimited by said first moveable plate shearing surface and by said second moveable plate shearing surface, said movable plate dimensioned for being inserted into said gap in an insertion direction and for defining a first shearing plane between said first plate shearing surface and said first moveable plate shearing surface and for defining a second shearing plane between said second plate shearing surface and said second movable plate shearing surface, said moveable plate being displaceable in said gap in said insertion direction into a soil sample loading position in which said moveable plate through hole is coaxially aligned with said blind hole and said second plate hole.

* * * * *